United States Patent
Apple et al.

[19]

[11] Patent Number: 6,117,064
[45] Date of Patent: Sep. 12, 2000

[54] CATHETER SYSTEM

[76] Inventors: Marc G. Apple, 1606 Sycamore Hills Dr., Fort Wayne, Ind. 46804; Melvin J. Apple, 2553 NW. 52nd St., Boca Raton, Fla. 33496

[21] Appl. No.: 09/003,383

[22] Filed: Jan. 6, 1998

Related U.S. Application Data

[60] Provisional application No. 60/035,761, Jan. 6, 1997.

[51] Int. Cl.[7] .............................. A61N 5/00; A61M 3/00; A61M 29/00
[52] U.S. Cl. .............................. 600/3; 606/192; 606/194; 600/1; 600/4
[58] Field of Search .................................. 600/1, 3, 4, 5; 606/7, 192, 194; 604/93, 27, 96, 97, 99, 101, 104

[56] References Cited

U.S. PATENT DOCUMENTS

| | | |
|---|---|---|
| 5,059,166 | 10/1991 | Fischell et al. .............................. 600/3 |
| 5,213,561 | 5/1993 | Weinstein et al. ........................... 600/3 |
| 5,302,168 | 4/1994 | Hess ............................................ 600/3 |
| 5,411,466 | 5/1995 | Hess ............................................ 600/3 |
| 5,429,582 | 7/1995 | Williams ..................................... 600/3 |
| 5,611,767 | 3/1997 | Williams ..................................... 600/3 |
| 5,616,114 | 4/1997 | Thornton et al. ............................ 600/3 |
| 5,662,580 | 9/1997 | Bradshaw et al. ........................... 600/3 |
| 5,840,008 | 11/1998 | Klein et al. ................................. 600/3 |
| 5,913,813 | 6/1999 | Williams et al. ............................ 600/3 |
| 5,951,458 | 9/1999 | Hastings et al. ............................ 600/3 |

FOREIGN PATENT DOCUMENTS

| | | |
|---|---|---|
| 0688580 | 12/1995 | European Pat. Off. . |
| 9304735 | 3/1993 | WIPO . |

*Primary Examiner*—Cary O'Connor
*Assistant Examiner*—Navin Natnithithadha
*Attorney, Agent, or Firm*—Richard J. Godlewski

[57] ABSTRACT

A catheter apparatus filled with a radiation carrier material such as an inert radioactive gas for the treatment of restenosis after angioplasty, and malignancies. The inflated catheter includes a plurality of discrete chambers for transporting the radioactive carrier material, and a plurality of discrete chambers enabling substantial blood flow through the artery during treatment with the prescribed radiation. The inflated catheter may also comprise one unit balloon. A specific metal coating enhances the radiation dose delivered to the target. The wall of the lumen attenuates transmission dose to the blood circulating through the hollow inner lumen of the catheter device. The system also creates increased by-product radiation, from the impact of beta particles and gamma protons traveling toward the lumen wall. In addition, two opposing balloons may be utilized that are inflatable in sequence enabling gas-tight redirection of radioactive gas flow from one balloon to the other, where one balloon is inflated to deliver a treatment dose, while the opposing balloon is deflated.

19 Claims, 8 Drawing Sheets

CATHETER SYSTEM

CROSS-REFERENCE TO RELATED APPLICATIONS

This application claims priority of provisional application Ser. No. 60/035,761 filed Jan. 6, 1997. This application is also related to copending application Ser. No. 08/748,698 filed Nov. 13, 1996.

TECHNICAL FIELD

The invention relates to catheter systems for administering radiation to patients.

BACKGROUND OF THE INVENTION

Angioplasty is an established procedure for reducing the effect of atherosclerotic plaque on the arterial walls within the vascular system of the patient. The effect is reduced by use of a catheter that is inserted into the site of the diseased-occluded vessel. A balloon portion of the catheter is then inflated to a predetermined pressure range and size, to radially compress the plaque occlusion, thereby increasing the internal diameter of the previously restricted artery. The balloon is then collapsed and the catheter is removed.

After the angioplasty procedure has been performed, about one-third to one-half of the patients soon develop restenosis. Restenosis is the condition which may occur after angioplasty or other recannulation procedures, with or without stenting, wherein the proliferation of cells cause a restenotic lesion to form, resulting in the further blockage of the intravascular structure.

Radiation is administered to patients for a variety of reasons, such as to treat restenosis, malignant or benign tumors, or the like. Examples of such treatments are disclosed in U.S. Pat. Nos. 5,059,166; 5,213,561; and 5,302,168.

It would be preferred to be able to provide a radiation system which would:

a) deliver a predetermined totally-cumulative and homogeneous dose of radiation to the lesion site, at a predetermined penetration depth, while minimizing the exposure of surrounding healthy tissue to the radiation;

b) enable the treating physician or other health-care personnel to be bedside to the patient during the administration of the radiation therapy without exposing the physician or health care personnel to any unreasonable risk;

c) use radiation material that is readily and inexpensively available from a commercial provider;

d) use minimal special equipment storage, or delivery devices, except for routine facilities available in most nuclear medicine or radiation oncology departments;

e) use a radiation carrier material that if applied as an unsealed free-gas form, the inert, noble gas properties essentially enable the molecules of the carrier material to rapidly dissipate throughout the body of the patient without any prolonged organ accumulation or chemical interaction, and rapid dilution of the carrier material is quickly re-released from the bloodstream through the lungs;

f) minimize long term occlusion of normal blood flow during therapy, thereby providing more flexibility as to administration time and dosage;

g) use a radiation carrier material that is a stable and which can be pressurized, stored, and made to high millicurie activity per cubic centimeter with reasonable cost and availability;

h) use beta particles having excellent initial dose rate delivery and energy transfer when directly adjacent to the targeted tissue within the first one millimeter, and not penetrate much beyond this depth;

i) use gamma photon energies having depth doses that provide complementary dose deposition with the beta particles for the first one millimeter, and primary additive dose delivery for an additional two to three millimeters of the targeted tissue;

j) use these beneficial physical and biological radiation properties for treating restenosis, and malignancies (for example—in the brain, lung, esophagus, trachea, cervix, biliary ductal system, colon or rectum, the gastrointestinal system, the gynecological system, or head and neck) and other internal ailments where an internal application of radiation directly applied to the tissue may be needed; and k) attenuate the transmission dose to blood circulating through the apparatus, and while creating increased by-product radiation, delivering useful radiation dose over hundreds of micrometers of target tissue.

SUMMARY OF THE INVENTION

The foregoing problems are solved and a technical advance is achieved in an illustrative catheter system of the present invention. The system of the present invention is useful for the administration of ionizing or other types of therapeutic radiation. The intravascular catheter system of the present invention uses either of several unique radiation carrier fluids. The catheter apparatus preferably includes a plurality of balloon sections although a single balloon unit may be employed, which is inflatable by an inert radioactive carrier fluid (liquid or gas). Residual blood or other body fluid flows through the artery or tube and the catheter when the balloon sections are deflated and inflated. When the balloon(s) are inflated, the blood flows through a plurality of sections disposed between and/or within the balloon sections. The system can also be readily modified for tissue or organ-specific design to treat malignancies in passageways or tubes of cancer patients, or even injecting the catheter into tissue.

In one embodiment of the present invention, one catheter can perform the two functions of angioplasty as well as the treatment of restenosis. The radioactive fluid can initially be used to expand the balloon section, to perform the angioplasty, and then left in situ to prevent or minimize restenosis. Alternatively, the initial expansion for the angioplasty can be performed by introduction of a discrete fluid, which will then be removed and replaced by the radioactive fluid.

As a further alternative, the angioplasty catheter can, after it has fulfilled its normal function, be withdrawn and replaced by the catheter apparatus described herein. A lesser number of changes of catheter is better for the patient, since any intrusion into coronary arteries can be damaging.

The catheter is designed to be capable of direct insertion into any tumor or to be maneuverable into a position adjacent to a tumor such as by being maneuverable into a body cavity or along a body passageway through which body fluids will pass. When the catheter is used in a vein or artery, capacity should be made to permit the flow of blood within the catheter such as between and/or inside the balloon or balloons or to maintain perfusion flow via the central lumen, and provision is made such as by shielding or variable balloon(s) thicknesses to provide radiation shielding for the blood. Certain body fluids will obviously not require radiation shielding.

The balloon section can either comprise a single balloon or a plurality of balloons arranged on the catheter section either peripherally or longitudinally or both. The section is inflated by the radiation fluid and that causes the exterior parts of the balloon or balloons to improve the contact with the tissue. There can be an exterior inflatable coating of the catheter movable into contact with the tissue or the contact can be direct between the balloon(s) and the tissue. The wall of the balloon(s) in the region of the tissue is of reduced thickness in order to maximize the radiation to the tissue. The thickness obviously must be sufficient to prevent leakage of radiation fluid. The stronger the radiation, the more important the question of leakage becomes.

The treatment method of the present invention may be applied to a patient either after angioplasty has been performed, or for treating malignant tissue within the brain, lung, esophagus, trachea, cervix, biliary ductal system, colon or rectum, the gastrointestinal system, the gynecological system, or head and neck.

The method is designed to apply ionizing radiation prophylactically to post-angioplasty vascular tissue or tumors internal to a patient while minimizing exposure of healthy tissue. Initially, the location and the size of the tissue to be treated are clinically identified, perhaps, with a fluoroscope. The catheter apparatus is then introduced and positioned adjacent to or within the tissue to be treated. The catheter apparatus is then inflated by the radioactive fluid (e.g., gas) thereby exposing the tissue to radiation. The catheter may include a plurality of discrete balloon sections with special and hypo-dense material, which enable the inflated catheter to match more closely the internal tissue wall, and minimize the amount of gas loss internal to the patient in the event of leakage. The catheter apparatus includes an outer retractable radiation sleeve or shield to prevent the exposure of healthy tissue to radiation. The radiation shield is then retracted to a specific measurable length. Preferably, the radioactive fluid is an inert gas, such as xenon or an isotope of xenon, and emits beta and gamma particles into the tissue to be treated.

A specific coating of integrated and layered transitional metal or metal alloy compounds from the surface to the center of the gas exposed side of the wall of the central catheter lumen enhances the radiation dose delivered to the targeted tissue. The wall of the lumen attenuates transmission dose to the blood circulating through the hollow inner lumen of the catheter device. Also, the system creates increased by-product radiation, from the impact of beta particles and gamma photons traveling toward the lumen wall. This energy would otherwise be wasted as treatment dose, but instead produces by-product low-energy x-ray photons which increase the deposited energy dose into the target tissue via scattered angle coincidence or secondary redirected x-ray production from the slowing of beta particles traveling into the metal compound on the wall surface. The by-product x-rays travel through the balloon outer wall and deliver useful radiation dose to the targeted tissue (Bremsstrahlung).

Two opposing and separate, semi-circular balloons include opposed support displacers attached just proximal and distal to the balloon lengths, upon the outer lumen wall. The built-in injection port unit enables gas-tight redirection of radioactive gas flow from one balloon to the other, one balloon being inflated and delivering treatment dose, while the opposing balloon is deflated. The support displacers are juxtaposed against the vessel wall enabling blood to flow more easily through the space opposite to the treatment side. For a more complete understanding of the catheter system of the present invention, reference is made to the following detailed description and accompanying drawings in which the presently preferred embodiments of the invention are shown by way of example. As the invention may be embodied in many forms without departing from spirit of essential characteristics thereof, it is expressly understood that the drawings are for purposes of illustration and description only, and are not intended as a definition of the limits of the invention. Throughout the description, like reference numbers refer to the same component throughout the several views.

DETAILED DESCRIPTION

FIGS. 1 to 6 disclose the preferred embodiment of the delivery system 10 of the present invention which comprises a supply of radioactive fluid or gas 12 and a catheter apparatus 20. Preferably, the balloon catheter apparatus 20 is made of latex or similar synthetic compound, commonly used for intravascular applications, and void of any silicon-based or other metal-based materials. The catheter apparatus is disposable after each patient use, and is designed to handle peak expected pressures less than those used in conventional angioplasty. The pressures range from one to ten atmospheres.

As used herein, the term "fluid" includes any gas, liquid, or gel-type substance that generally conforms to the shape of the container within which it is held, and is fluent. While the catheter apparatus of the present invention is used in conjunction with a radioactive carrier fluid, it is preferred that the fluid is a gas, and for reasons hereinafter set forth, an inert gas, such as preferably xenon, or an isotope of xenon. However, the present invention is not limited to xenon gas or an isotope thereof, and the preferred fluid includes all gases and isotopes thereof, radioactive gases or radiogases (inert and/or non-inert) or gases capable of fluorescence, phosphorescence, or luminescence (electron stimulation). Examples of gases include, but are not limited to, xenon, krypton, neon, radon and their isotopes. A radiogas can be dissolved in a liquid or solution (sterile) and be used as a liquid radiofluid. Liquids include all isotopes of liquids and solutions. An isotope can be radioactive or non-radioactive. Radioactive includes nuclear (nucleus) decay of an atom. A radionuclide is any radioactive atom. Fluorescence, phosphorescence or luminescence is associated with electron instability and subsequent emission of radiant energy. Liquids also include all gases dissolved in liquids or solutions. Examples of liquids include, but are not limited to, liquid phosphorus, rhenium, yttrium, technetium, iodine, gallium, chromium, strontium, thallium, samarium, ytterbium, palladium, and all isotopes thereof, and all compounding and binding solutions thereof. All gels utilizing the aforementioned gases or liquids (solutions) are also contemplated. Additional radionuclides can include osmium, vanadium, ruthenieum, bismuth, or other transitional heavy metals and their isotopes for liquid and/or gel-type compounding. All inert dual photon/electron emitting radionuclides are further contemplated as well as all inert single particle radio-emitting nuclides and all non-inert radionuclides thereof. Still further contemplated are all inert or non-inert radiofluids which use electron stimulation to produce by-product fluorescent, phosphorescent or luminescent radiant energy for patient treatment. The use of by-product radiant energy emissions including fluorescent, phosphorescent or luminescent emissions can be utilized for therapeutic treatment. Implementation of radionuclide and by-product radiant energy emissions can be applied by the use of the catheter apparatus in the following combinations;

(A) gases and/or fluids or single fluids alone either as a gas-gas or gas-liquid, and/or either inert or non-inert; and/or radioactive or non-radioactive; such that the photon or electron emissions of one radiofluid can induce electron shift, scatter, or a quantum level change in the electron shell of the same or other combined "fluid" atoms thereby causing production of relatively low energy photon/electron (possibly in a cascaded amplification) emissions into the targeted tissue as a controlled/calculated dose;

(B) radiofluid(s) as described in "A", except that induction of listed radiant energy is provided via electrical source stimulation from an electrode, cathode, wire or other transmission source such that controlled electrical currents and/or electrical potential delivered through the catheter to the radiofluid or non-radiofluid of the balloon catheter which causes expected electron excitation and/or quantum level fluctuations with by-product fluorescence, phosphorescence and/or luminescence for the aforementioned therapeutic treatments; and (C) phosphorus and/or other known fluorescent metals or alloys are implanted in the balloon material and/or catheter structure so that the combinations described in (A) and (B); radioemission, by-product decay energy and/or direct electrical stimulation can cause effect on the implanted/layered materials so as to create fluorescent, phosphorescent or luminescent energy delivery as these materials stabilize their electron structure after such stimulation.

The unique intravascular catheter system 10 of the present invention uses a radiation carrier fluid. The catheter apparatus 20 preferably includes a plurality of balloon sections 22, 24, and 26 which are inflated with the radioactive carrier material. Residual blood flows through the artery when the balloon sections 22, 24, and 26 are inflated through a plurality of interposed sections 32, 34, and 36 disposed between the balloon sections.

Figures 1, 2, 3:
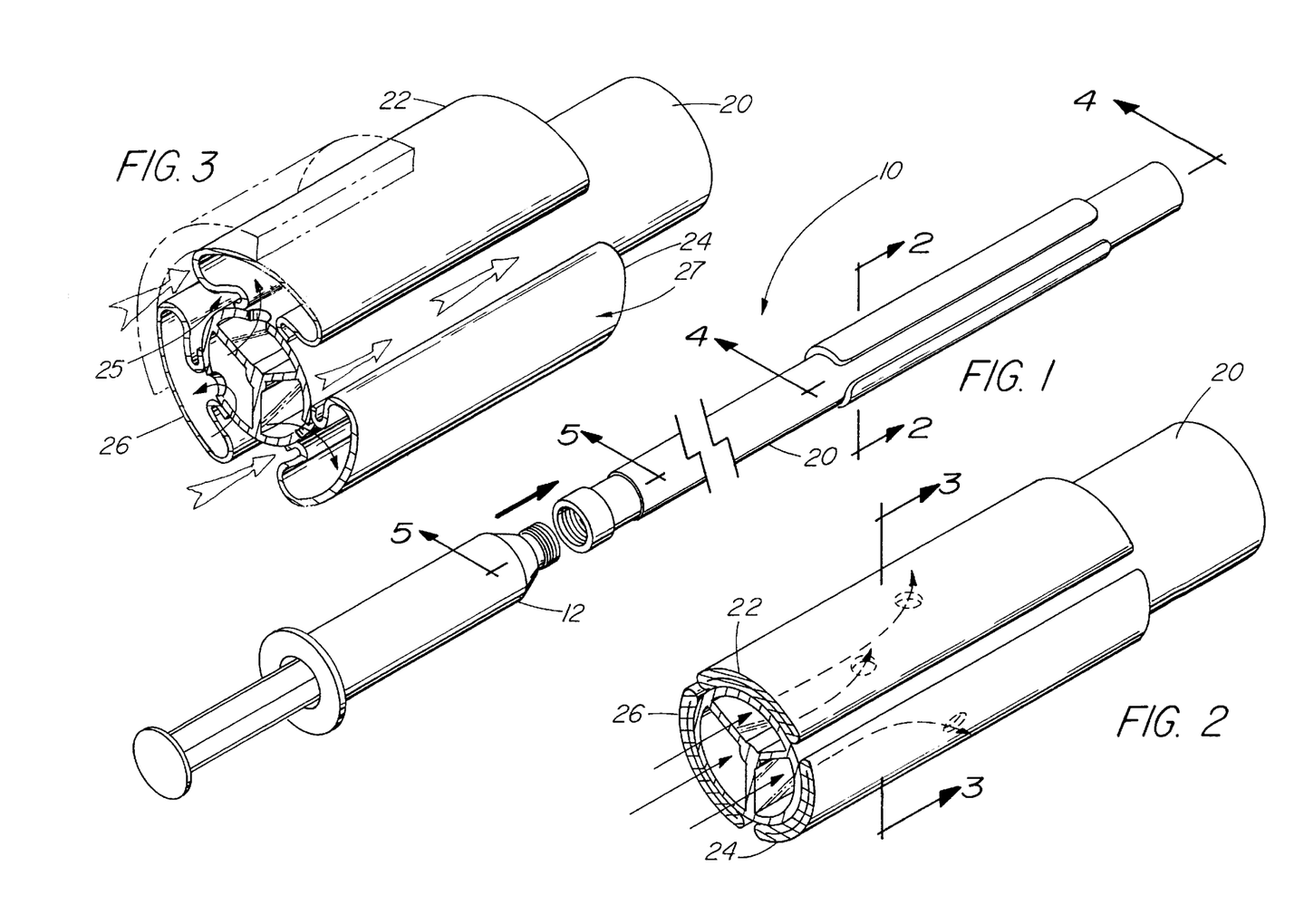
FIG. 1 is an assembly drawing of the preferred embodiment of the catheter system of the present invention.
FIG. 2 is a detail sectional view of the deflated catheter apparatus taken along line 2—2 of FIG. 1.
FIG. 3 is a detail sectional view of the fully-inflated catheter apparatus taken along line 3—3 of FIG. 2.
Figure 4:
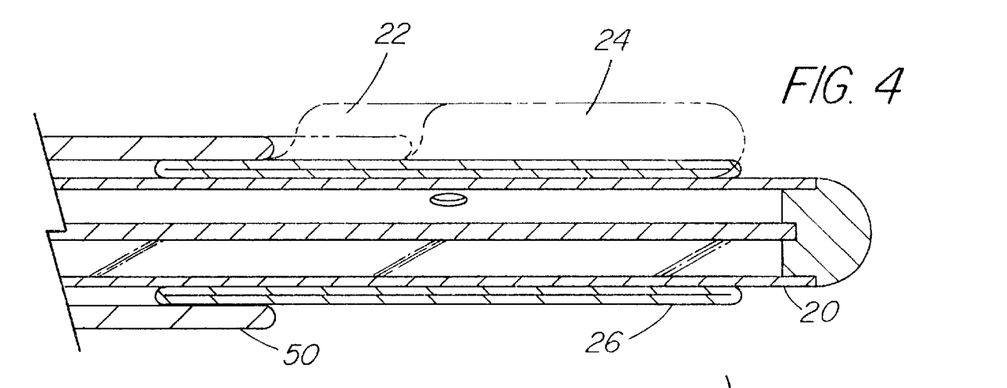
FIG. 4 is a detail sectional view of the deflated catheter apparatus taken along line 4—4 of FIG. 1.
Figure 5:
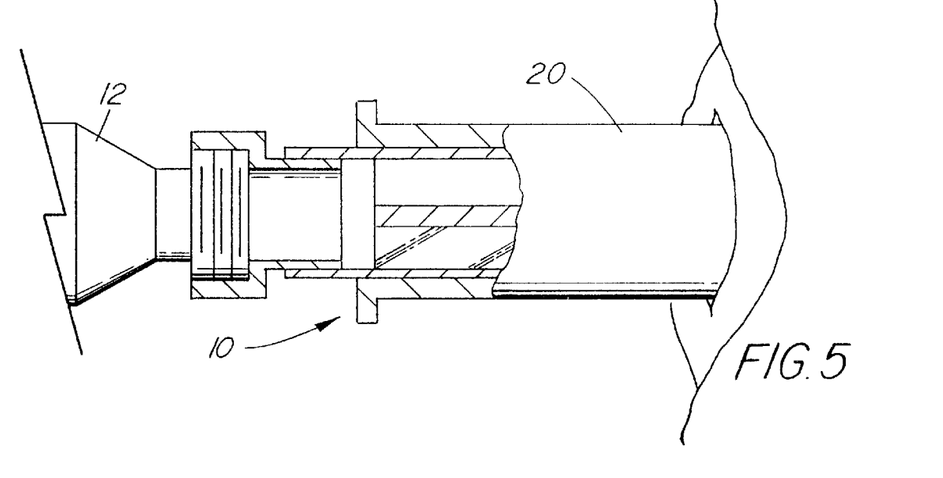
FIG. 5 is an enlarged sectional view of the engagement between the protected, syringed gas supply and the catheter apparatus of FIG. 1.
Figure 6:
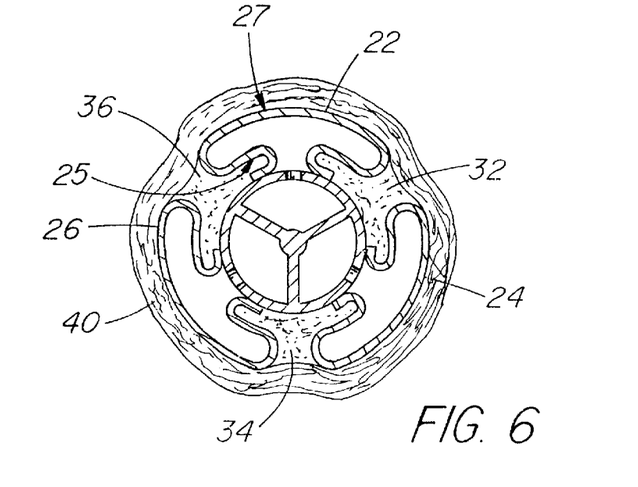
FIG. 6 is a detail sectional view of the fully-inflated catheter apparatus as shown in FIG. 1 inside an arterial wall.

The method is designed to apply ionizing radiation prophylactically to post-angioplasty vascular tissue or tumors disposed internally within a patient while minimizing exposure of healthy tissue. Initially, the location and the size of the lesion 40 to be treated are clinically identified, perhaps, with a fluoroscope. The catheter apparatus 20 is then introduced and positioned adjacent to the lesion 40. The plurality of discrete balloon sections 22, 24, and 26 of a special, hypo-dense, thin material enable the inflated catheter apparatus 20 to more closely match the internal tissue wall, and minimize the amount of internal gas loss in the event of leakage. The catheter apparatus 20 includes an outer retractable radiation sleeve or shield 50 to prevent the exposure of healthy tissue adjacent to the lesion to radiation. After the catheter apparatus 20 is positioned alongside the lesion 40, the radiation shield 50 is retracted to a specific measurable length. The balloon sections 22, 24, and 26 are then inflated with the radioactive fluid exposing the lesion 40 to the radiation dosage. The preferred gas, xenon or xenon isotope, emits beta and gamma particles into the lesion 40.

Figure 7:
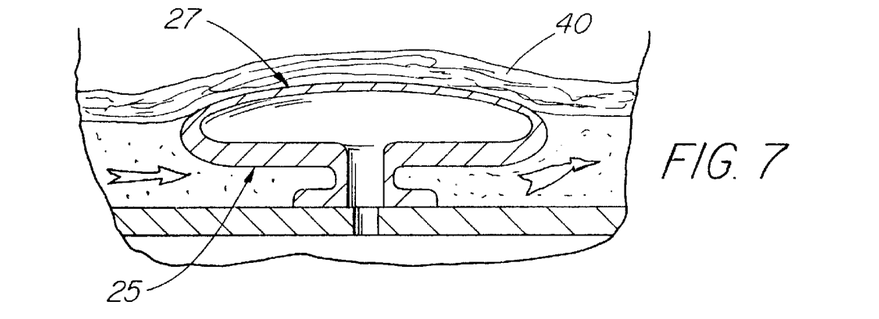
FIG. 7 is a second embodiment disclosing a detail sectional view of a balloon of a catheter apparatus being fully-inflated and having a thickened interior wall and a thinner, hypo-dense outer wall.

The catheter apparatus 20 enables substantial blood or other fluid flow between the balloon sections 22, 24, and 26 when fully inflated. The balloons sections 22, 24, and 26 include a unique inner and outer surface 25 and 27 configuration. The radiation flow is directed through the outer surface 27 of the catheter apparatus 20 to the lesion 40 while exposure to radiation of the blood flowing internal to the catheter apparatus 20 is minimized. Accordingly, the inner surface 25 is more attenuating to the transmission of radiation than the outer surface 27. Either the inner surface (wall) 25 is thicker than the outer surface (wall) 27 as shown in FIG. 7, or the inner surface 25 includes a layer of material that is resistant to the penetration of radiation (not shown).

Figures 8, 9:
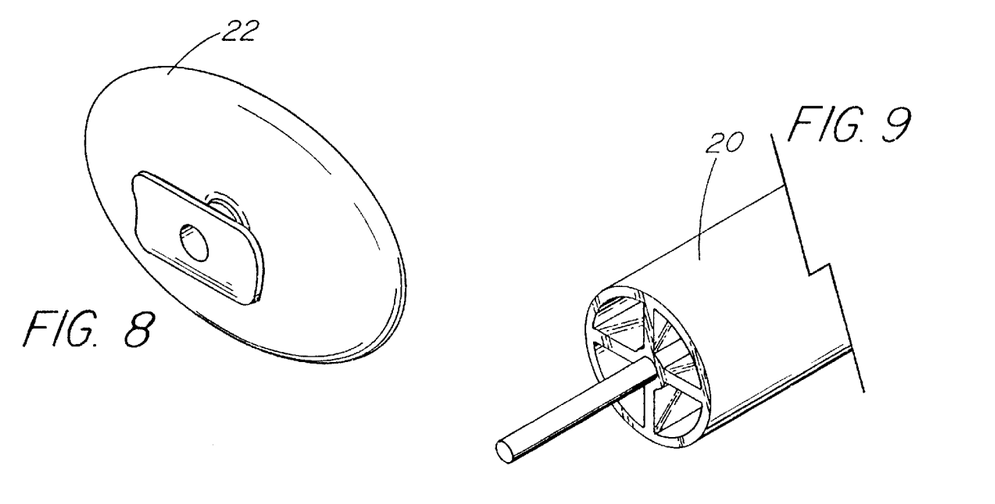
FIG. 8 discloses a detail of an inflated balloon of the catheter apparatus shown in FIG. 7.
FIG. 9 discloses a third embodiment of the catheter apparatus having a removable central lumen guide/localizing wire that is radio-opaque.
Figure 10:
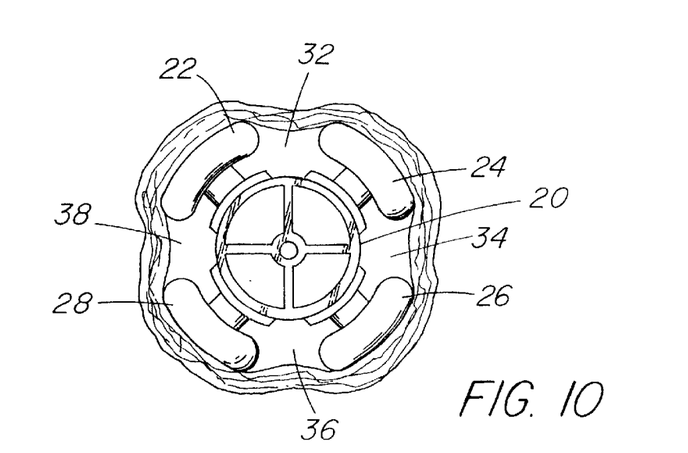
FIG. 10 is a detail sectional view of the fully-inflated catheter apparatus of FIG. 9 within the arterial wall.
Figure 11:
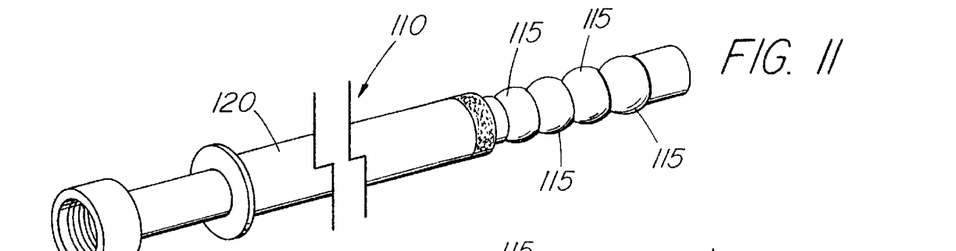
FIG. 11 is an assembly drawing of a fourth embodiment of the catheter system of the present invention with the catheter apparatus being deflated.
Figure 12:
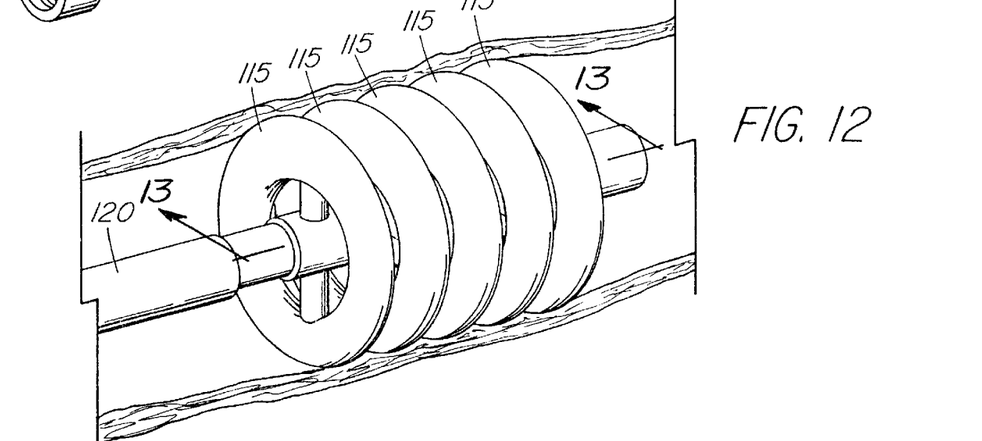
FIG. 12 discloses a detail view of the fully-inflated catheter apparatus of FIG. 11.
Figure 13:
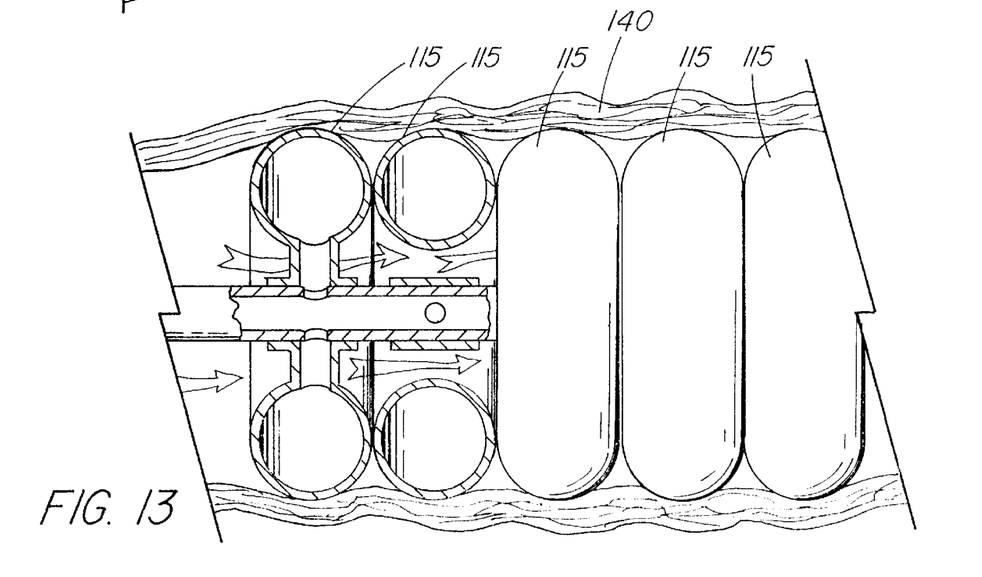
FIG. 13 is a detail sectional view of the fully-inflated catheter apparatus taken along line 12—12 of FIG. 12.
Figure 14:
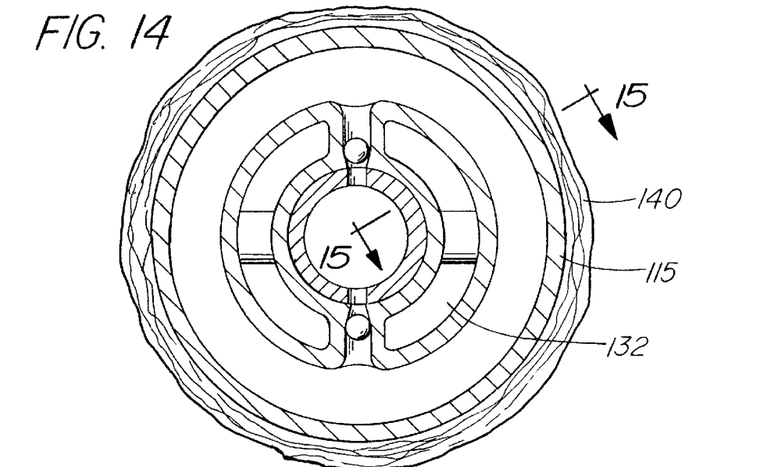
FIG. 14 is a detailed sectional view of the fully-inflated catheter apparatus of FIG. 11.
Figure 15:
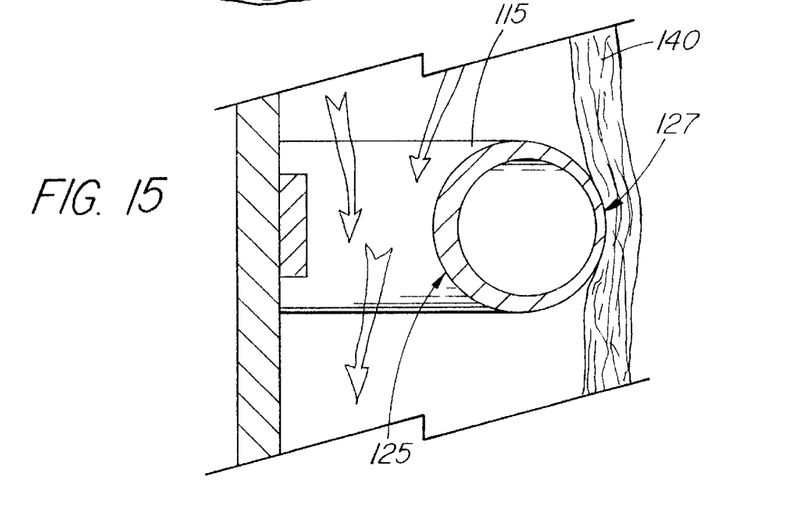
FIG. 15 is an exploded sectional view of a fully-inflated balloon of the catheter apparatus of FIG. 14, the balloon having a thickened inner wall and a thinner hypo-dense outer wall.

Preferably, either three discrete balloon sections are used as shown in FIGS. 1 through 6, or four balloon sections 22, 24, 26, and 28 with interposed sections 32, 34, 36, and 38 can be used as shown in FIGS. 9 and 10.

One primary application of the system of the present invention is for use after standard, angioplasty procedure; including multiple lesions at one treatment session. Controlled internal radiation therapy is provided to an artery or vessel for the prevention of arterial restenosis due to smooth muscle hyperplasia or similar related pathology. This will enable cannulation via the same access port from the preemptive dilatation procedure.

Discrete balloon sections or segmented systems 22, 24, and 26 or possible variants thereof are specifically structured to enable the application of a radioactive gas for therapeutic intent.

FIGS. 11 through 16 disclose another embodiment of the catheter apparatus 120 of the present invention. Drafted segmental and peripheral "tire-like" balloon sections or segment configurations 115 optimize direct circumferential abutment of the entire lumen wall. This will minimize intraluminal attenuation factors and maximize homogeneous dose rate delivery, conforming and enabling irregularly-shaped intimal surfaces. Also, when the catheter segments 115 are pressurized and expanded, a significant residual rate of intraluminal blood flow is enabled internal to the segments.

The catheter apparatus of the present invention is designed to minimize the secondary risk of medical complications caused by blood flow deficiency due to underlying disease or vasospasm in the peripheral, kidney, and, particularly, the heart vessels. The centrally directed perfusion flow may also contribute to outwardly directed pressure gradients, therefore, further supporting and stabilizing the radioactive-gas expander balloons against the arterial wall.

The catheter apparatus of the present invention enables individual patient flexibility as to dosage, treatment exposure time, and lesion segment lengths. Also, since blood flow is not completely occluded during therapy, radiation time need not be limited to less than three minutes, and therefore, very high energy gamma emitters or radiation activity levels are not needed. More expensive loading devices, shielded treatment rooms, and solid radio sources are thereby avoided. Also, healthy tissue is not unnecessarily exposed to passing or placement-preparation time irradiation as with other solid-source systems.

If inadequate blood flow rates or distal symptoms occur, this closed, sealed and inert radioactive gas system 10, 110 may be easily deflated without exposing the patient or medical personnel to real radiation risk. After flexibly allowing for several minutes of reperfusion time, the catheter apparatus 20, 120 may be simply reinflated and the prescribed treatment time/dose (several times if needed) is resumed without diminishing the therapeutic prophylactic benefit.

Furthermore, the system of the present invention enables the treating therapeutic radiologist to address more than one vessel system or lesion even distal to the distribution of the primary lesion that may require subjective variation in post-dilatation balloon length and diameter due to sensitivity of distal ischemic-prone tissue from risk of prolonged diminished blood flow.

The sectioned, segmented or compartmentalized radioactive gas delivery tracks communicating with the end point expander balloons, will minimize the potential volume of gas leak should a balloon lose integrity. The residual catheter gas volume may be withdrawn into the shielded syringe without further leakage. The bloodstream released gas poses no real radiation or chemical threat to the patient, because of the physical and biological properties of the inert gas.

Figure 16:
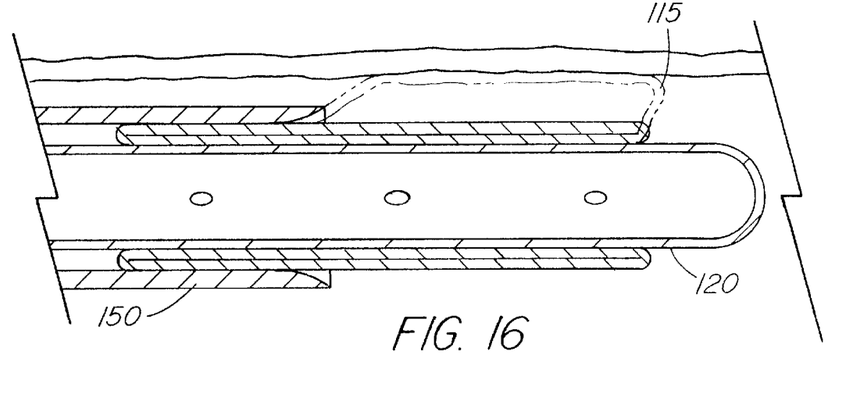
FIG. 16 is a detailed sectional view of the partially-inflated catheter apparatus of FIG. 11, complete with the retractable sleeve.

The length of the distal expandable component of the catheter apparatus 20 or 120 is covered by a thin, retroslidable or static sleeve 50 or 150, as shown in FIGS. 4 and 16, which is radio-opaque for purposes of imaging localization. The sleeve 50 or 150 is in direct continuity with and manipulatable externally by the physician. The sleeve is positioned proximal the access port to the balloon sections or segments. After confirmation of placement of the distal catheter apparatus 20 or 120 by fluoroscopic means, the catheter sleeve 50 or 150 is slowly pulled back, and a concordant ruler is exposed in parallel, measured in millimeters, whereby the treating physician accurately determines the length of balloon to be expanded, and the length of the vessel wall to be treated 40 or 140. This will enable immediate confirmatory calculations as to specific dose rates, treatment time, and the volume of the radioactive gas injected.

The proposed radioactive gas or gases emit gamma photons enabling imaging and semi-log calculations to be performed at bedside using a conventional gamma camera and computer (not shown), which is left on the monitor distal to the treatment field to detect any early leakage for concerned physicians at minimal additional cost.

Although the lumen diameter is narrow and contains only a small fraction of the total volume of radioactive gas injected per session, the designed shielding properties of the sleeve 50 or 150 or outer lumen wall layer minimize any significant normal tissue or blood cell exposure over the remaining non-inflated catheter length, particularly with the energies of emission of the isotopes selected.

The interval and possibly staggered placement design of the entry portals and columns between the catheter body and expansion "modules" or balloons; enable cutoff control of the balloon expansion length due to the controlled length of outer sleeve retraction.

The primary rationale and benefits for the therapeutic application of radioactive xenon gas with the "ASP" or similar catheters for intravascular brachytherapy enable precise determination of total dose, dose rate, and depth distribution of radiation emitted from a source.

Radioactive xenon-133 gas, and less commonly used xenon-127 gas and krypton 85, as well as technetium compounds, have been widely used for several years and proven relatively safe within medically accepted radiation levels for nuclear diagnostic studies involving the lung and the measurement of blood and fluid flow rates through vessels to specific organs. When used as an unsealed free-gas form, the inert, noble gas properties essentially enable the molecules to rapidly dissipate throughout the body of the patient or through a room, without any prolonged organ accumulation or interaction within specific dose ranges. Rapid expulsion of the relatively lower energy nuclear emissions of the xenon, is quickly re-released from the bloodstream through the lungs.

Xenon is a very stable element which can be pressurized, stored, and made to high millicurie activity per cubic centimeter with very reasonable cost and availability.

Xenon-133 provides both a beta particle (101 kev avg.; 364 kev max.), and at least two usable photons (32 kev 48 percent; 81 kev 37 percent).

The beta particles offer excellent initial dose rate delivery when directly adjacent to the tissue with the first millimeter. The particle does not penetrate much further beyond the first millimeter of tissue, thereby not contributing to any significant distal normal tissue exposure.

The gamma photon energies and their decay fractions provide complementary dose deposition for the first millimeter, and primary dose delivery for an additional several millimeters of arterial wall and adjacent tissue. The high percent of attenuated, and lower energy photons beyond this point provide for ease of personnel protection with routine lead jackets, or by placing a cover over the external surface of the treated region. Furthermore, the sensitivity of a small field gamma camera provides simple image monitoring and dose evaluation simultaneously.

Xenon-133 is commercially available within a week in concentration ranges from 10 mci to 150 mci per cc or more of gas volume. Also, the cost is currently estimated to be less than a few hundred dollars a dose of 150 mci. A single dose order may be used to treat several patients per day for a full week, as the physical half-life is 5.2 days. Also, no special equipment, storage, or delivery devices are necessary, except for routine facilities available in most nuclear medicine or radiation oncology departments.

In vivo, and in vitro facilities with standard exhaust hoods or negative pressure rooms provide adequate protection for this sealed use of xenon gas. A metered dose can safely and readily be transported to nearly any treatment site by one person, and administered by one person without special radiation protection needs, such as is necessary with higher energy photon sources for conventional brachytherapy. The most expensive addition to a standard treatment room is a simple negative pressure ventilation system, as a backup safety mechanism.

Figure 17:
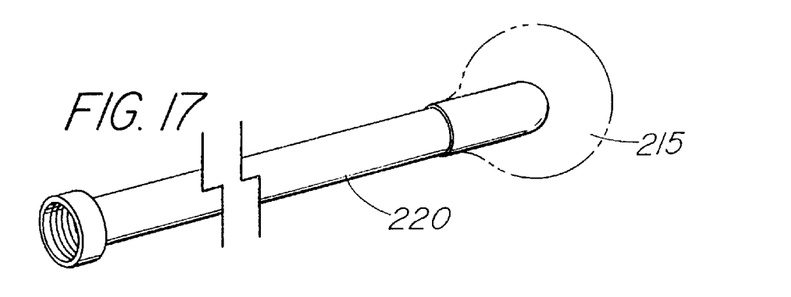
FIG. 17 is a fifth embodiment of the present invention disclosing a deflated catheter apparatus for use in treating malignancies in an organ such as the brain, esophagus, lung, or colon.
Figure 18:
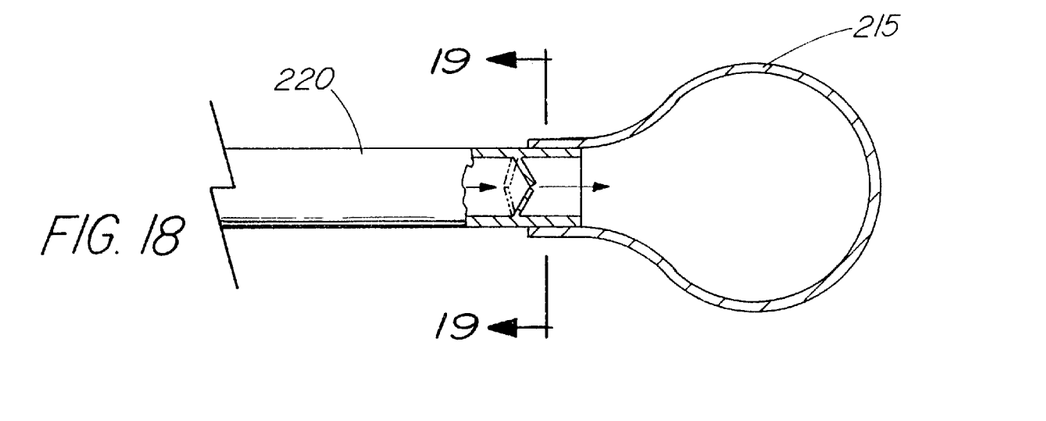
FIG. 18 is a detail view of the inflated catheter apparatus of FIG. 17.
Figure 19:
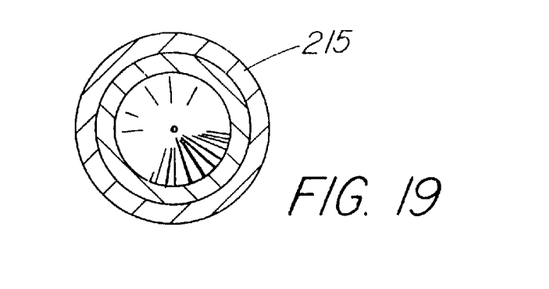
FIG. 19 is a detail sectional view of the pressure-sensitive flapper valve for the inflated catheter apparatus taken along line 19—19 of FIG. 18.

Balloon shaping and customizing design with various thickness and pliable lucent and radio penetrable material enable site specific, intracavity or intraparenchymal insertion and localization from external origin and placement. FIGS. 17, 18, and 19 illustrate various other applications for the catheter apparatus 220 which may include brain, lung, esophagus, trachea, cervix, biliary ductal system, colon or rectum, the gastrointestinal system, the gynecological system, and head and neck. All would optimize the self-introduction of radioactive xenon-133 or others, with controlled expansion and dose rate delivery while enabling individual tissue compliance such that the entire tissue is immediately and homogeneously adjacent to this high or low dose rate source without requiring surgical implant disruption, patient isolation, use of high energy concentrations of other radio nuclides, patient or medical personnel risk from leakage, expensive materials, or costly radio-safe suite facilities.

The compliance, stress, and thickness properties of the balloons enable adequate and complete volume expansion against the variable surface of the arterial wall at less pressure than conventional therapeutic dilation plasty catheters.

Figures 20, 21:
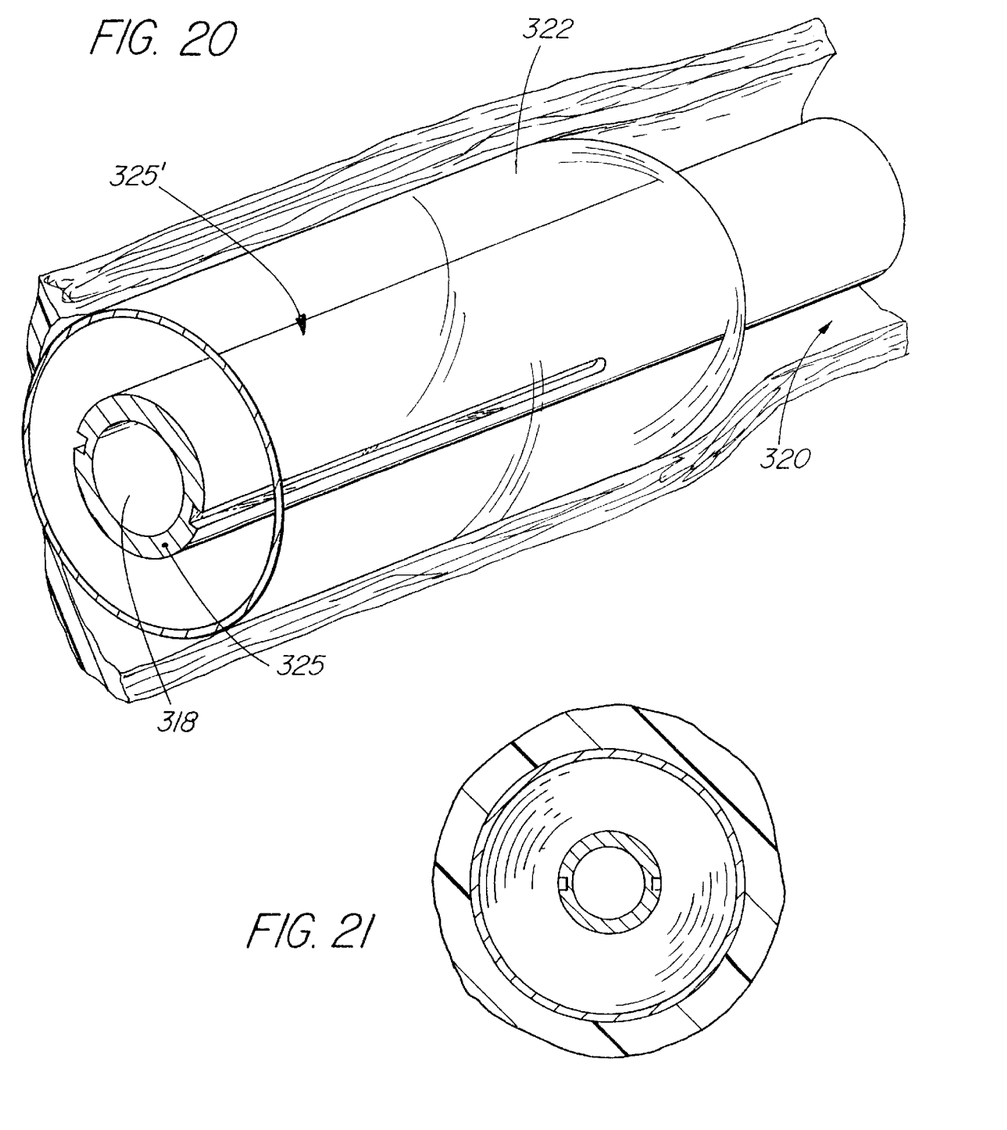
FIG. 20 is an enlarged assembly drawing of a sixth embodiment of the catheter system of the present invention, with a single balloon fully inflated as the blood flows through the center section of the apparatus.
FIG. 21 is a end view of the catheter system of FIG. 20.

FIGS. 20 and 21 disclose yet another embodiment of the catheter apparatus 320, the catheter comprising an inner lumen 318 (with wall 325) for the transmission of blood when the catheter is inserted into a blood vessel. A specific coating of integrated and layered transitional metal or metal alloy compounds from the surface to the center of the exterior side 325' of the wall of the catheter lumen 318 protects the blood in the lumen from radiation, and enhances the radiation dosage delivered to the target. Either the heavy transitional metals or denser ranges of heavy metals are recommended, such as titanium, tungsten, aluminum, and germanium. The alloys may also include silicon. As used herein, the term "metal" includes pure metals, metal alloys, and metal alloy compounds.

FIG. 20 shows a balloon 322 extending around the inner lumen, and expanded by radiation fluid, the expanded balloon being in contact with the internal wall of a blood vessel. The lumen wall 325 attenuates the transmission dosage to the blood circulating through the hollow inner lumen of the central catheter apparatus 320. In addition, the system creates increased by-product radiation, Bremsstrahlung and incidental scatter, from the impact of beta particles and gamma photons traveling into or toward the lumen wall 325. This energy which would otherwise be wasted produces by-product low-energy x-ray photons which increase the deposited energy dosage into the target tissue via scattered angle coincidence or secondary redirected x-ray production from the slowing of beta particles traveling into or next to the metal compound on the wall surface 325'. These particles might ordinarily be considered too far from or having too little energy to reach the target tissue. However, the by-product x-rays (Bremsstrahlung Radiation) travel through the balloon outer wall and deliver useful radiation dosage over a range of several hundred micrometers to the targeted tissue.

Figures 22, 23:
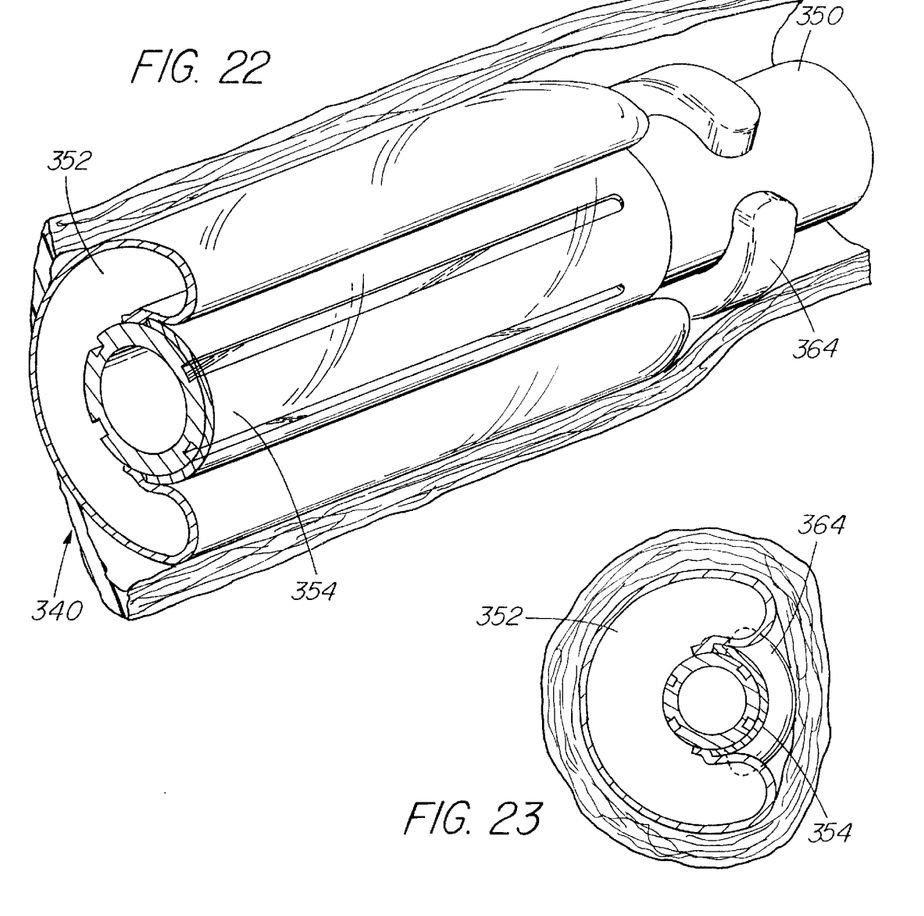
FIG. 22 is an enlarged assembly drawing of a seventh embodiment of the catheter system of the present invention, with two separate, semi-circular balloons, one balloon being inflated and delivering treatment dose, while the opposing balloon is deflated.
FIG. 23 is a end view of the catheter system of FIG. 22.
Figure 24:
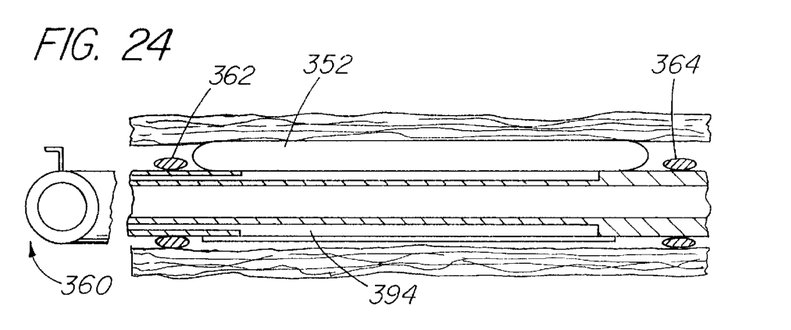
FIG. 24 is a side view of the catheter system of FIG. 22.

Still another catheter apparatus 340 is disclosed in FIGS. 22, 23 and 24. Two opposing and separate, semi-circular balloons 352 and 354 include opposed support displacers 362 and 364 attached just proximal and distal to the balloon lengths, upon the outer lumen wall 350 of the inner lumen.

An injection port unit 360 enables fluid-tight redirection of radioactive fluid flow from between the balloons 352 and 354. Thereby, while one balloon 352 is inflated and delivering treatment dosage, the opposing balloon is deflated 354. The support displacers 362 and 364 are juxtaposed against the vessel wall enabling blood to flow more easily through the space opposite to the treatment side.

The single-unit injection port 360 with synthetic septum is fluid-tight and leak-proof. The port 360 is preferably made of Viton rubber, enabling easy needle penetration without loss of gas under pressure via leaky adaptive lever-lock additions.

The radioactive xenon gas may be partially dissolved in sterile saline or lipid-containing solution for solubilizing the xenon. The resulting material may then be injected into a balloon system.

What is claimed is:

1. Catheter apparatus for irradiating internal tissue of a patient, wherein the catheter apparatus comprises means for connection to a supply of radioactive gas; wherein the catheter apparatus is capable of being inserted either into, or adjacent to, the said tissue; and wherein the catheter apparatus comprises a balloon section, at least part therof being inflatable by the radioactive gas in order to correctly locate the radioactive gas relative to the said tissue; and wherein the said balloon section when inflated with the radioactive gas is structured to conform and to provide homogeneous radiation delivery to the said tissue.

2. Catheter apparatus according to claim 1, wherein the balloon section comprises either a single balloon or a plurality of balloons, each being inflatable at the outer periphery of the catheter apparatus, each balloon being connectable to and inflatable by the radioactive gas.

3. Catheter apparatus according to claim 2, wherein each of the said plurality of balloons is arranged either around a respective peripheral part of the catheter apparatus, or along a respective longitudinal part of the catheter apparatus.

4. Catheter apparatus according to claim 2, wherein the catheter apparatus is designed for location within a body passageway, and wherein each balloon is inflatable so as to contact the wall of the passageway.

5. Catheter apparatus according to claim 4, wherein each balloon has an inner surface and an outer surface, and wherein the outer surface of each balloon enables optimal penetration of the said tissue by radiation.

6. Catheter apparatus according to claim 5, wherein the inner surface of each balloon increases the attenuation of the radiation penetrating by body fluid in the said passageway.

7. Catheter apparatus according to claim 1, wherein the catheter balloon section is designed for post-angioplasty or other recannulation procedures for minimizing restenosis, or for treating malignant diseases or benign hyperproliferative type diseases.

8. Catheter apparatus according to claim 1, wherein the catheter is designed for the treatment or prevention of restenosis.

9. Catherer apparatus according to claim 1, further comprising a radioactive gas from at least one of a group consisting of krypton, neon, radon, or xenon gas or an isotope thereof.

10. Catheter apparatus according to claim 1, wherein the radioactive gas is designed to emit at least one of beta and gamma particles.

11. Catheter apparatus according to claim 6, wherein the inner surface of each balloon includes at least one of a cross-section thicker than said outer surface and of an increased attenuation material.

12. Catheter apparatus according to claim 1, wherein the catheter further comprises a movable shield designed to protect body parts adjacent to the said tissue.

13. Catheter apparatus according to claim 1, wherein the catheter has a catheter wall which includes a metallic based material.

14. Catheter apparatus according to claim 13, wherein the metal material is at least one of a specific layer of a heavy transitional metal, and of a metal selected from titanium, germanium, tungsten, aluminum, a titanium alloy, a germanium alloy, a tungsten alloy, and an aluminum alloy.

15. Catheter apparatus according to claim 13, wherein the balloon section comprises one part to be inflated while another part is to be simultaneously deflated.

16. Catheter apparatus according to claim 1, wherein the radioactive gas, is induced in the balloon to undergo electron stimulation, whereby by-product fluorescent, phosphorescent, and/or luminescent radiant energy for therapeutic purposes can be produced.

17. Catheter apparatus according to claim 1, wherein the catheter apparatus has at least one of an injection and a directional entry port which minimizes risk of gas leakage and allows for directional control of radioactive gas.

18. Catheter apparatus according to claim 1, wherein the catheter system includes means for electrical conductance or potential to be applied to an inflated balloon.

19. Catheter apparatus for irradiating internal tissue of a patient, wherein the catheter apparatus comprises means for connection to a supply of radioactive gas; wherein the catheter apparatus is capable of being inserted either into, or adjacent to, the said tissue; and wherein the catheter apparatus comprises a tissue compliant balloon section, at least part thereof being inflatable by the radioactive gas in order to correctly locate the radioactive gas relative to the said tissue and to deliver a homogeneous radiation dose and/or homogenous radiation dose rate.

* * * * *